United States Patent [19]

Fainzilberg

[11] 4,198,679
[45] Apr. 15, 1980

[54] METHOD AND DEVICE FOR DISCRIMINATING THERMAL EFFECT OF PHASE TRANSFORMATION OF METALS AND ALLOYS IN THE PROCESS OF THEIR COOLING

[75] Inventor: Leonid S. Fainzilberg, Kiev, U.S.S.R.

[73] Assignee: Institut Kibernetiki Akademii Nauk Ukrainskoi SSR, Kiev, U.S.S.R.

[21] Appl. No.: 920,121

[22] Filed: Jun. 28, 1978

[30] Foreign Application Priority Data

Jun. 28, 1977 [SU] U.S.S.R. ............................. 2500835
Jul. 8, 1977 [SU] U.S.S.R. ............................. 2509754

[51] Int. Cl.$^2$ ...................... G06F 15/20; G01N 25/02
[52] U.S. Cl. ................................ 364/497; 73/17 R; 75/130 R; 364/557
[58] Field of Search ............... 364/497, 499, 496, 500, 364/472, 557; 75/59, 60, 130 R, 132, 133, 129; 73/17 R, 341, 359, 360, 361; 324/103 R, 103 P, 104

[56] References Cited

U.S. PATENT DOCUMENTS

| | | | |
|---|---|---|---|
| 3,329,495 | 7/1967 | Ohta et al. ...................... | 364/497 X |
| 3,475,599 | 10/1969 | Schwartzenberg et al. ..... | 364/500 X |
| 3,816,720 | 6/1974 | Bauer ............................... | 364/500 |
| 3,891,834 | 6/1975 | Warsinski ......................... | 364/497 |
| 4,088,974 | 5/1978 | Zhitetsky et al. ............... | 364/499 X |

*Primary Examiner*—Joseph F. Ruggiero
*Attorney, Agent, or Firm*—Haseltine, Lake & Waters

[57] ABSTRACT

A method and apparatus for discriminating the thermal effect of phase transformation of metals and alloys in the process of their cooling, by measuring the temperature of a metal or alloy being cooled, the time elapsed from the beginning of the temperature measuring cycle and the duration of a temperature arrest occurring in the process of the metal or alloy cooling. The measured duration of the temperature arrest is compared with a threshold of the temperature arrest duration for making a decision ascertaining the occurrence of the thermal effect of phase transformation if the measured duration of the temperature arrest exceeds the threshold of duration of the temperature arrest. The method further includes measuring an increment of temperature of a metal or alloy being cooled relative to the maximum temperature recorded during the temperature measuring cycle, calculating a threshold of duration of the temperature arrest as a function of temperature of the metal or alloy being cooled, and measuring increments of these temperatures relative to the maximum temperature recorded during the temperature measuring cycle. The time elapsed from the beginning of the temperature measuring cycle is metered with the threshold value of the temperature arrest duration calculated for the moment of occurrence of temperature arrest, being used for the comparison.

2 Claims, 32 Drawing Figures

METHOD AND DEVICE FOR DISCRIMINATING THERMAL EFFECT OF PHASE TRANSFORMATION OF METALS AND ALLOYS IN THE PROCESS OF THEIR COOLING

FIELD OF THE INVENTION

The present invention relates to physicochemical research in metals and alloys in the metallurgy and, in particular, to a method and device for discriminating the thermal effect of phase transformation of metals and alloys in the process of their cooling.

This invention can be employed in thermographic analysis of phase transformation of metals and alloys for determining the temperature of phase transformation. In addition, the present invention can also be used for determining other parameters of metals and alloys, associated with the temperature of phase transformation, and in particular, for determining the carbon content in a molten steel in the process of its production by the temperature at the beginning of the crystallization (liquidus temperature).

DESCRIPTION OF THE PRIOR ART

In thermographic analysis of metals and alloys there arises a problem of discriminating the thermal effect of phase transformation with reference to temperature arrests in the process of cooling of metals and alloys. The difficulties in solving this problem lie in that, in practice, apart from the temperature arrests caused by the thermal effect of phase transformation, there also occur temperature arrests as a result of accidental disturbances such as, for example, sharp changes in the heat exchange conditions, i.e. so-called pseudothermal effects.

In this connection, it becomes necessary to discriminate the thermal effect of phase transformation in the presence of psuedothermal effects. The reliability of discriminating the thermal effect can be defined as the probability of making a false decision, by the false decision being implied both ascertaining the occurence of the thermal effect of phase transformation on the basis of a temperature arrest caused by the pseudothermal effect and ascertaining the absence of the thermal effect of phase transformation on the basis of a temperature arrest caused by the true thermal effect of phase transformation. A method of discriminating the thermal effect of phase transformation of metals and alloys in the process of their cooling is known in the prior art, employing a device for determining the carbon content in a molten metal with reference to temperature arrests in cooling curve (See GDR Accepted Application No. 120713, British Pat. No. 1477564).

The method comprises measuring such parameters as the temperature of a metal or alloy being cooled, the time elapsed since the start of the temperature measuring cycle, the duration of a temperature arrest, and comparing the measured duration of the temperature arrest with a predetermined threshold of the duration of the temperature arrest and making decision ascertaining the presence of the thermal effect of phase transformation on the basis of the results of comparison if the measured duration of the temperature arrest exceeds the predetermined threshold of the duration of the temperature arrest.

A device for carrying out the above method comprises a converter for converting temperature into a digital pulse code, which is fed through its input with a signal containing information on the temperature of a metal or alloy being cooled, a clock pulse generator, a synchronizer for distributing in time code and clock pulses, a reversible counter for generating a temperature parallel code, a threshold counter for determining local increments of the temperature, a time interval counter provided with information output which contains information on the time metered from the next successive moment when a local increment of the temperature assumes a predetermined value. A signal is formed at an overflow output thereof in case the time exceeds a predetermined threshold of the temperature arrest duration. A cycle counter having information output with information on the time elapsed since the start of the temperature measuring cycle. A flip-flop is provided for memorizing a signal occurring at the moment of making a decision ascertaining the occurrence of the thermal effect of phase transformation, and a register for storing a parallel code of temperature.

The outputs of the converter for converting temperature into a digital pulse code, code pulses corresponding to a positive and a negative increments of temperature and are connected respectively to a first and a second inputs of the synchronizer, with an output of the clock pulse generator being connected to a third input of the synchronizer. The first output of the synchronizer is adapted to deliver synchronized code pulses corresponding to a positive increment of temperature, is connected to add inputs of the reversible and threshold counters. The second output of the synchronizer, for delivering synchronized code pulses corresponding to a negative increment of temperature and is connected to the subtract inputs of the reversible and threshold counters. An output of the synchronized clock pulses of the synchronizer is connected to the count inputs of the time interval counter and of the cycle counter.

The overflow outputs of the threshold counter have pulses formed at the moment when a predetermined local increment of temperature occurs and are connected to initial setting inputs of the time interval counter. An overflow output of said time interval counter is connected to the control input of the register and to a setting input of the flip-flop. An information input of said register is connected to an information output of the reversible counter. An output of the flip-flop is electrically coupled with count blocking inputs of the threshold counter and of the time interval counter.

During metal or alloy cooling, the code pulses from the outputs of the converter for converting temperature into a digital pulse code, after having been synchronized with the clock pulses in said synchronizer, are fed depending on the sign of the temperature increment, either to the subtract inputs or to the add inputs of the reversible and threshold counters, respectively. As a result, the reversible counter generates a parallel code of temperature and at the overflow outputs of the threshold counter pulses at the instant of time when a local increment of temperature assumes a predetermined value $\pm\epsilon_o$. These pulses are applied to the initial setting inputs of the time interval counter which counts synchronized clock pulses arriving at its count input. The time interval counter is constructed so that at its overflow output, a pulse is formed in case the time interval between two successive moments of the pulse arrival at its inputs of initial setting, exceeds a predetermined threshold $\tau_o$ of the temperature arrest duration.

Thus, prior to an accurrence of the temperature stop, no pulse is formed at the overflow output of the time interval counter. When a temperature arrest occurs, no pulses are formed at the overflow outputs of the threshold counter, because the local increment of temperature does not exceed $\pm\epsilon_o$ value. If the temperature arrest duration is in excess of the predetermined threshold $\tau_o$ of the temperature arrest duration, the time interval counter will overflow, a pulse from the overflow output of said counter will be fed to the control input of the register. In this case, the latter is supplied with a code of the liquidus temperature delivered from the reversible counter. At the moment of making a decision ascertaining the occurrence of the thermal effect of phase transformation, the signal arriving from the flip-flop output will block both the threshold counter and the counter of time intervals. As the predetermined time from the beginning of the temperature measuring cycle elapses, there is a signal at the information output of the cycle counter indicative of the termination of the temperature measuring cycle.

Thus, making a decision ascertaining the occurrence of the thermal effect of phase transformation with the use of the above method and device. This is done by comparing a measured duration $\tau$ of the temperature arrest with the predetermined threshold $\tau_o$ of the temperature arrest duration.

In practice, there are cases when a temperature arrest caused by the thermal effect of phase transformation is of the same duration as the temperature arrest caused by the pseudothermal effect.

In these cases, it is known in the art to not allow such temperature arrest to be distinguished from each other. Thus, this method does not provide for a sufficient reliability in discriminating the thermal effect of phase transformation.

SUMMARY OF THE INVENTION

The principal object of this invention is to provide a method for discriminating the thermal effect of phase transformation of metals and alloys in the process of their cooling which, by using additional information on the parameters of metal cooling, improves the reliability in discriminating such effect.

Another object of the invention is to provide on the basis of simple units used in a digital computing technique employing a device for determining the thermal effect of phase transformation of metals and alloys in the process of their cooling which employs additional information on the parameters of cooling, and can improve the reliability in discriminating the effect.

These and other objects of the invention are attained by the proposed method and apparatus for discriminating the thermal effect of phase transformation of metals and alloys in the process of their cooling, by measuring the temperature of a metal or alloy being cooled, the time elapsed from the beginning of the temperature measuring cycle, and the duration of a temperature arrest occurring in the process of the metal or alloy cooling. The measured duration of the temperature arrest is compared with a threshold of the temperature arrest duration for making a decision ascertaining the occurrence of the thermal effect of phase transformation if the measured duration of the temperature arrest exceeds the threshold of duration of the temperature arrest. The method further includes measuring an increment of temperature of a metal or alloy being cooled relative to the maximum temperature recorded during the temperature measuring cycle, calculating a threshold of duration of the temperature arrest as a function of temperature of the metal or alloy being cooled, and measuring increments of these temperatures relative to the maximum temperature recorded during the temperature measuring cycle, and metering the time elapsed from the beginning of the temperature measuring cycle is metered with the threshold value of the temperature arrest duration calculated for the moment of occurrence of temperature arrest, being used for the comparison.

These and other objects of the invention are also attained in a device for carrying out the above method, comprising a converter, for converting temperature into a digital pulse code, which is fed through its input with a signal containing information on the temperature of metal or alloy being cooled, a synchronization unit for distributing in time code and clock pulses, having inputs connected to outputs of said converter, at which outputs there appear code pulses corresponding to positive and negative increments of temperature, and to an output of a clock pulse generator, a reversible counter, for generating a parallel code corresponding to a measured temperature, having its add and substract inputs connected to outputs of the synchronization unit, at which outputs there appear synchronized pulses corresponding to positive and negative increments of temperature, a threshold counter for determining temperature local increments, having add and subtract inputs connected to said outputs of the synchronization unit, and to a count blocking input of which is applied a signal at a moment when the thermal effect of the phase transformation is ascertained, whereas at its first and second overflow outputs there are formed pulses at moments when local positive or negative temperature increments assume a predetermined value, a counter of time intervals metered starting from a moment when a local temperature increment assumes a predetermined value, the counter having a count input connected to a synchronized clock pulse output of the synchronization unit, and initial setting inputs connected to overflow outputs of the threshold counter. To the count blocking input of the time interval counter there is applied a signal at a moment when the thermal effect of the phase transformation is ascertained, and a main register, for storing a parallel code of metal or alloy temperature, has an information input connected to an information output of the reversible counter. A main control input has a signal applied to control entering information into said main register, a cycle counter, for metering the time elapsed since the start of the temperature measuring cycle, has a count input connected to the synchronized clock pulse output of the synchronization unit, and an information output whereat there appears information on the time elapsed since the start of the temperature measuring cycle. The proposed device further includes according to the invention, an additional register for storing a parallel code of a time interval elapsed from the start of the temperature measuring cycle to the next successive moment when the local increment of temperature assumes a predetermined value, having an information input connected to the information output of the cycle counter, and control inputs connected to overflow outputs of the threshold counter, a temperature increment counter for determining a temperature increment relative to the maximum temperature recorded during the temperature measuring cycle, having a count input connected to the second overflow output of said threshold counter, a selector of signs of the thermal effect of phase transformation, having inputs connected to the information outputs of the main register, of the temperature increment counter of the additional register, and of the time interval counter, and an output connected to the count blocking inputs of the threshold counter and of the time interval counter, with the main and the additional control inputs of said main register, being connected to the overflow outputs of said threshold counter.

The use of additional information on the parameters of the process of cooling of metals and alloys by the above method and device, in accordance with the invention, allows the reliability of determining the thermal effect of phase transformation to be improved.

These and other objects and advantages of the invention will now be explained in greater detail with reference to embodiments thereof which are represented in the accompanying drawings, wherein:

Figure 9:
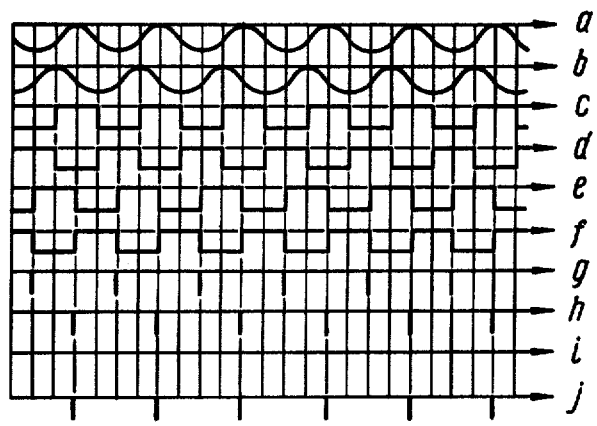
Figure 10:
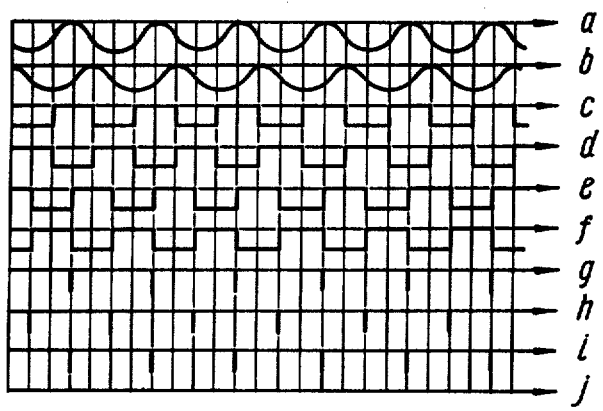
Figure 11:
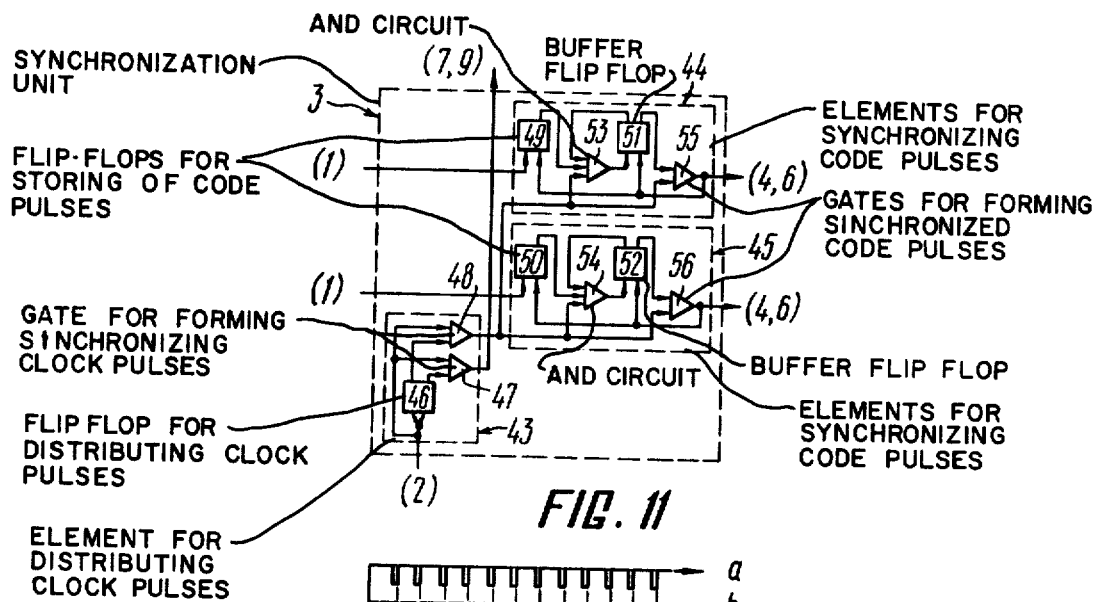
Figure 13:
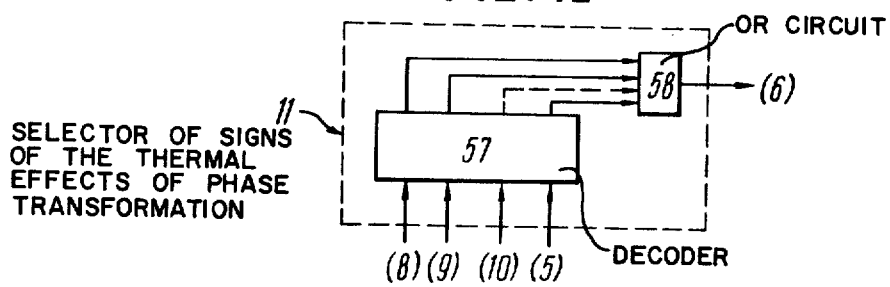

FIG. 9a, b, c, d, e, f, g, h, i, j are the time plots illustrating the operation of the converter of temperature into a digital pulse code with a positive increment of temperature, according to the invention;

FIG. 10 is substantially similar to that of FIG. 9 but with a negative increment of temperature;

FIG. 11 is a functional diagram of a synchronization unit, according to the invention;

FIG. 12a, b, c, d, e, f, g, h, i, j, k are time plots illustrating the operation of a synchronization unit, according to the invention;

FIG. 13 is a functional diagram of a selector of signs of the thermal effect of phase transformation, according to the invention.

DESCRIPTION OF THE INVENTION

A method for discriminating the thermal effect of phase transformation of metals and alloys in the process of their cooling will further be illustrated with the aid of a cooling curve which represents a graph of the temperature variation of a metal or alloy being cooled. A representative shape of the cooling curve is illustrated in FIGS. 1, 2, 3, 4, 5.

In the process of cooling a sample of the molten metal, there are measured a temperature T of the metal and time t elapsed since the start of the temperature measuring cycle. In addition, there is measured an increment $\Delta T$ of temperature of the metal being cooled relative to the maximum temperature $T_{max}$ recorded during the temperature measuring cycle. On the basis of the measured parameters taken in the aggregate, a threshold $\tau_0$ of the temperature arrest duration is continuously calculated with the following formula:

$$\tau_0 = F(T, \Delta T, t) \qquad (1)$$

The function F is determined beforehand on the basis of statistical processing of the real cooling curves of metal samples, where temperature arrest caused by the thermal effect of phase transformations and temperature arrest caused by the pseudothermal effect are determined. The use of known methods of the theory of statistical decisions allows this function to be selected such that a probability of false decisions is minimal. A function F may be given either analytically or in the form of a table.

As soon as a temperature arrest occurs on the cooling curve, its duration $\tau$ is measured. The measured duration $\tau$ of the temperature arrest is compared with a threshold value $\tau_0$ of the temperature arrest duration calculated for the moment when the temperature arrest occurs. If a duration $\tau$ of the temperature arrest exceeds $\tau_0$ value, a decision is made ascertaining the occurence of the thermal effect of phase transformation of a metal or alloy being cooled. In case the duration $\tau$ of the temperature arrest is less than a threshold $\tau_0$, a decision is made ascertaining the absence of the thermal effect of phase transformation, which is indicative of that this temperature arrest is caused by the pseudothermal effect.

The method will be further described by way of examples, in accordance with the invention.

In the table below there are given optimal values of a threshold $\tau_0$ obtained on the basis of statistical processing of cooling curves of molten steel samples for some values T, $\Delta T$, t in compliance with (1).

| T, °C. | $\Delta T$, °C. | t, sec. | $\tau_0$, sec. |
| --- | --- | --- | --- |
| 1510 | 4 | 5 | 4 |
| 1510 | 12 | 5 | 3 |
| 1510 | 12 | 2 | 6 |
| 1510 | 20 | 5 | 5 |
| 1510 | 12 | 12 | 6 |
| 1510 | 20 | 12 | 8 |
| 1525 | 4 | 5 | 6 |
| 1525 | 12 | 5 | 6 |
| 1525 | 12 | 2 | 8 |
| 1525 | 20 | 5 | 6 |
| 1525 | 12 | 12 | 8 |
| 1525 | 20 | 12 | 10 |

Relationship given in the above table is not to be considered as the only possible one.

EXAMPLE 1

A temperature arrest whose duration $\tau_1$ is 4 seconds is recorded at a temperature $T_1$ (FIG. 1) of metal, which is equal to 1510° C. A maximum temperature $T_{1max}$ recorded during a temperature measuring cycle is 1522° C., i.e. $\Delta T = 12°$ C. Time $t_1$ elapsed since the start of the temperature measuring cycle till the moment of occurrence of a temperature arrest, is 5 seconds. In accordance with the data illustrated in the Table, a threshold value $\tau_{o1}$ for the given parameters is 3 seconds. Consequently, in this case a decision is made ascertaining the occurrence of the thermal effect of phase transformation.

EXAMPLE 2

A temperature arrest whose duration $\tau_2$ is 4 seconds is recorded at the temperature $T_2$ (FIG. 2) which is equal to 1510° C. A maximum temperature $T_{2max}$ recorded during a temperature measuring cycle is 1530° C. Time $t_2$ elapsed since the start of the temperature measuring cycle is 5 seconds. In accordance with the data illustrated in the Table, a threshold value $\tau_{o2}$ for the given parameters is 5 seconds. Consequently, in this case, a decision is made ascertaining the absence of the thermal effect of phase transformation. With the given values of parameters of the temperature arrest caused by the thermal effect of phase transformation only such a temperature arrest will be recognized, whose duration exceeds 5 seconds.

EXAMPLE 3

A temperature arrest with a duration $\tau_3$ of 4 seconds is recorded at a temperature $T_3$ (FIG. 3) which is equal to 1510° C. A maximum temperature $T_{3max}$ recorded during the temperature measuring cycle is 1522° C. Time $t_3$ elapsed since the start of the temperature measuring cycle is 12 seconds. In accordance with the data illustrated in the Table a threshold value $\tau_{o3}$ for the given parameters is 6 seconds. Consequently, in this case a decision is made ascertaining the absence of the thermal effect of phase transformation.

EXAMPLE 4

A temperature arrest with a duration $\tau_4$ of 4 seconds is recorded at a temperature $T_4$ (FIG. 4) which is equal to 1525° C. A maximum temperature $T_{4max}$ recorded during the temperature measuring cycle is 1537° C. Time $t_4$ elapsed since the start of the temperature measuring cycle is 5 seconds. In accordance with the data illustrated in the Table a threshold value $\tau_{o4}$ for the given parameters is 6 seconds. Consequently in this case, a decision is made indicative of that there is no thermal effect of phase transformation.

EXAMPLE 5

A temperature arrest with a duration $\tau_5$ of 12 seconds is recorded at a temperature $T_5$ (FIG. 5) which is equal to 1525° C. A maximum temperature $T_{5max}$ recorded during the temperature measuring cycle is 1537° C. Time $t_5$ elapsed since the start of the temperature measuring cycle is 12 seconds. In accordance with the data illustrated in the Table a threshold value $\tau_{o5}$ for the given parameters is 8 seconds. Consequently in this case, a decision is made as certaining the occurence of the thermal effect of phase transformation.

A device for discriminating the thermal effect of phase transformation of metals and alloys in the process of their cooling, employing the above method, comprises a converter 1 for converting temperature into a digital pulse code (FIG. 6), a clock pulse generator 2, a synchronization unit 3, a reversible counter 4, a main register 5, a threshold counter 6, a cycle counter 7, an additional register 8, a time interval counter 9, a temperature increment counter 10, and a selector 11 of signs of a thermal effect of phase transformation. An input 12 of the converter 1 is connected to a temperature sensor, for instance, to a thermocouple (not shown). Outputs 13, 14 of the converter 1 are connected to a first and a second inputs of the synchronization unit 3, respectively, whose third input is connected to an output 15 of the clock pulse generator 2. A synchronized clock pulses output 16 of the synchronization unit 3 is connected to count inputs of the cycle counter 7 and of the time interval counter 9, an output 17 of the synchronization unit 3 is connected to add inputs of the threshold counter 6 and of the reversible counter 4, with an output 18 of the synchronization unit 3 being connected to subtract inputs of the threshold counter 6 and of the reversible counter 4. An information output 19 of the reversible counter 4 is connected to an information input of the main register 5. Overflow outputs 20, 21 of the threshold counter 6 are connected to control inputs of the main and of the auxiliary registers 5, 8 and to initial setting inputs of the time interval counter 9. An overflow output 21 of the threshold counter 6 is connected to an input of the temperature increment counter 10. An information output 22 of the cycle counter 7 is connected to an information input of the additional register 8. An information output 23 of the auxiliary register 8, an information output 24 of the time interval counter 9, an information output 25 of the temperature increment counter 10 and an information output 26 of the main register are connected to inputs of the selector 11 of signs of the thermal effect of phase transformation. An output 27 of the selector 11 of signs of the thermal effect of phase transformation is connected to count blocking inputs of the time interval counter 9 and of the threshold counter 6.

Figure 7:
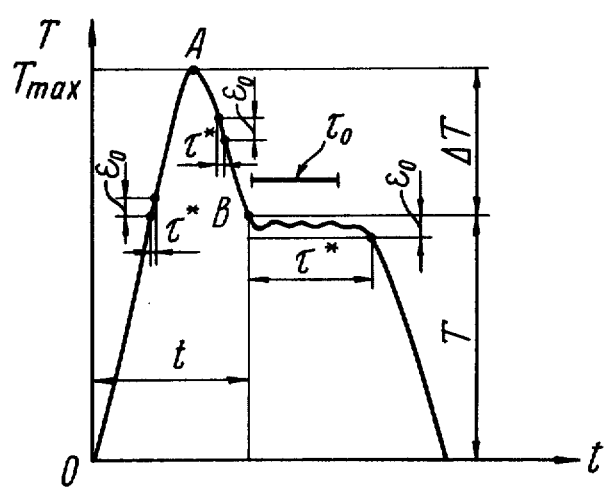
FIG. 7 is the cooling curve illustrating the operation of the device for discriminating the thermal effect of phase transformation of metals and alloys, according to the invention.

FIG. 7 shows a cooling curve illustrating the operation of the proposed device.

Figure 8:
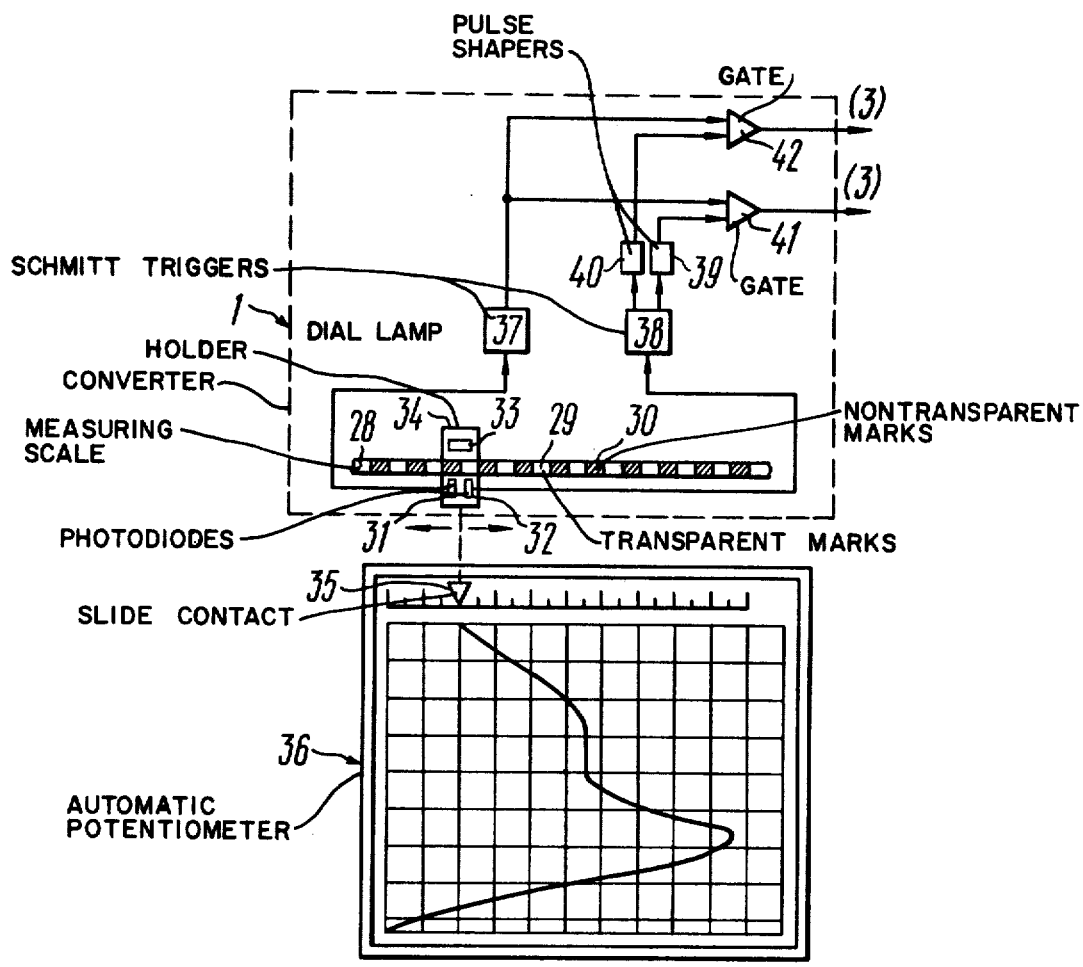
FIG. 8 is a functional diagram of a converter for converting temperature into a digital pulse code, according to the invention.

FIG. 8 shows a modification of the converter for converting an analogue signal into a digital pulse code, wherein an analogue signal is a signal containing information on the temperature of a metal being cooled. In this case an input 12 (FIG. 6) may be mechanically coupled, for example, with a slide contact of an automatic potentiometer continuously fed with a signal from a temperature sensor. The converter 1 (FIG. 8) includes a measuring scale where there are alternate transparent marks 29 and non-transparent marks 30 of equal widths. A number of the marks determines a resolving power of the converter 1. The converter 1 further includes two photodiodes 31, 32 and a dial lamp 33 which are mounted on a holder 34. The photodiodes 31 and 32 are spaced relative to each other within a distance equal to half the widths of the marks 29, 30.

The holder 34 of the converter 1 is mechanically coupled with the slide contact 35 of the automatic potentiometer 36.

In addition, the converter 1 comprises two Schmitt triggers 37, 38, two pulse shapers 39, 40 at a positive front of the signals arriving from outputs of the Schmitt trigger 38 and two gates 41, 42 for selecting code pulses corresponding to positive and negative increments of temperature on the cooling curve.

An input of the Schmitt trigger 37 is connected to an output of the photodiode 31 whereas an input of the Schmitt trigger 38 is connected to an output of the photodiode 32. A zero output of the Schmitt trigger 37 is connected to control inputs of the gates 41 and 42.

A unity output of the Schmitt trigger 38 is connected to an input of the pulse shaper 39 whereas the zero output of the Schmitt trigger 38 is connected to an input of the pulse shaper 40.

An output of the pulse shaper 39 is connected to a pulse input of the gate 41 whereas an output of the pulse shaper 40 is connected to a pulse input of the gate 42.

Code pulses of the converter 1 at outputs of gates 41, 42 are formed corresponding to positive and negative increments of temperature on the cooling curve.

This invention may be variously otherwise embodied.

FIGS. 9 and 10 illustrate time plots of the operation of the converter 1 with positive and negative temperature increments.

Figure 1:
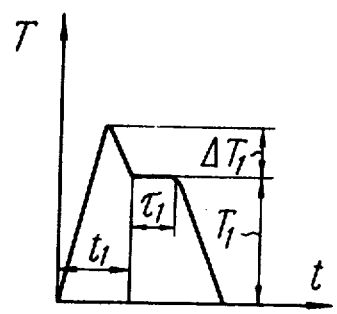
FIG. 1 is a typical cooling curve of a metal or an alloy, illustrating a method in accordance with the invention.
Figure 2:
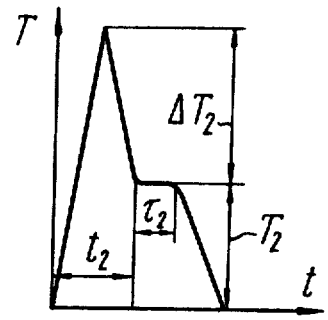
FIG. 2 is substantially similar to that of FIG. 1.
Figure 4:
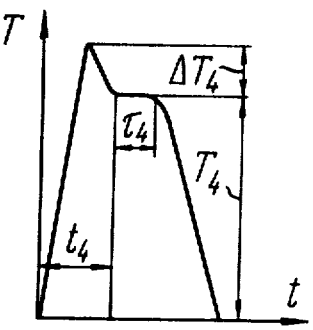
FIG. 4 is substantially similar to that of FIG. 1.
Figure 3:
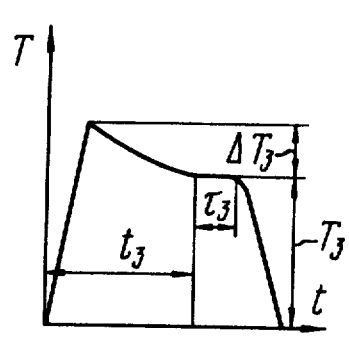
FIG. 3 is substantially similar to that of FIG. 1.
Figure 5:
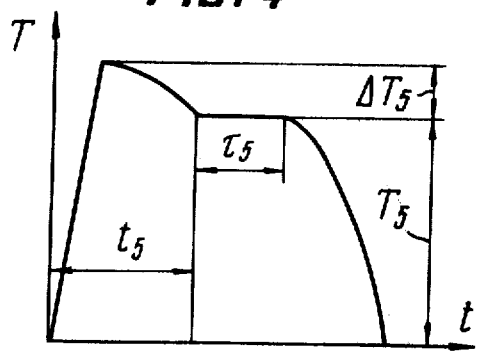
FIG. 5 is substantially similar to that of FIG. 1.
Figure 6:
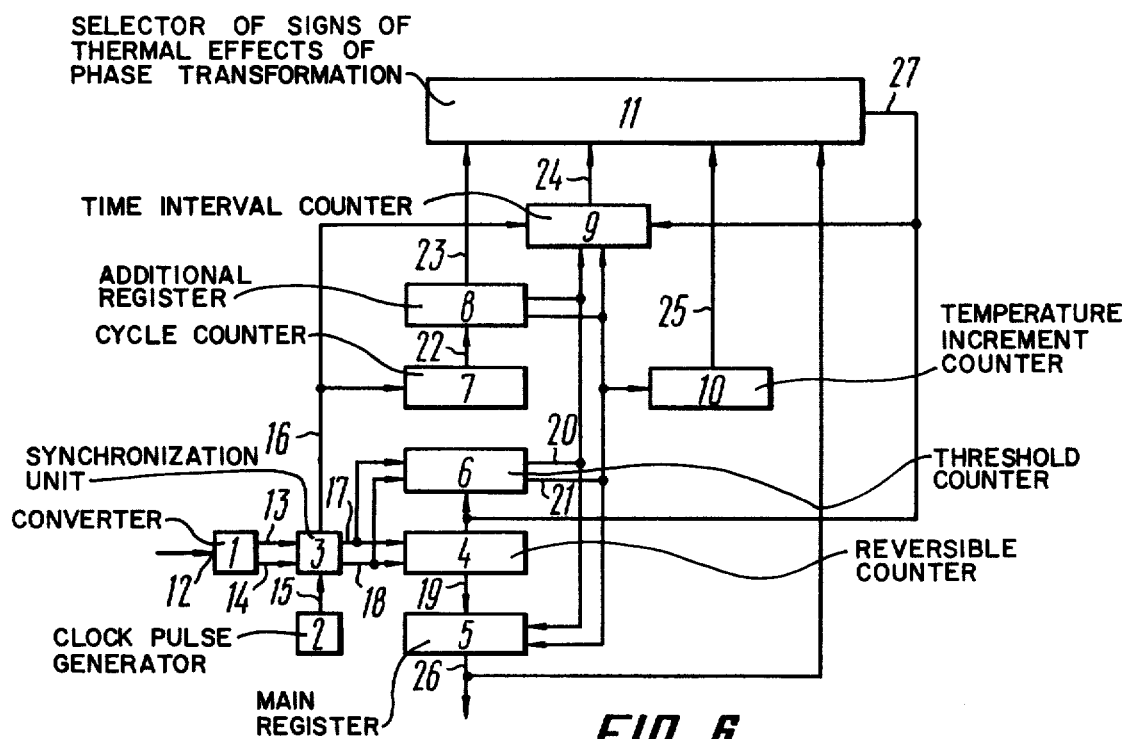
FIG. 6 is a block diagram of the device for discriminating the thermal effect of phase transformation of metals and alloys, according to the invention.

FIG. 11 is a preferred embodiment of a synchronization unit 3. The synchronization unit 3 includes an element 43 for distributing clock pulse and elements 44 and 45 for synchronizing code pulses. The element 43 for distributing clock pulses comprises a flip-flop 46 for distributing clock pulses, a gate 47 for forming synchronized clock pulses and a gate 48 for forming synchronizing clock pulses. Control inputs of the gates 47 and 48 are connected to outputs of the flip-flop 46. Pulse inputs of the gates 47 and 48 are interconnected and connected to a count input of the flip-flop 46, serving as an input of the synchronization 3, where there are applied pulses from a clock pulse generator 2 (FIG. 6). An output of the gate 47 (FIG. 11) is an output 16 (FIG. 6) of synchronized clock pulses of the synchronization unit 3. The elements 44 and 45 for synchronizing code pulses comprise flip-flops 49 and 50 for storing the code pulses, buffer flip-flops 51 and 52, AND circuits 53 and 54, gates 55 and 56 for forming synchronized code pulses.

A unit input of the flip-flop 49 is an input of the synchronization unit 3, where code pulses are applied corresponding to a positive increment of temperature on the cooling curve.

A unit input of the flip-flop 50 (FIG. 11) is an input of the synchronization unit 3, where code pulses are applied corresponding to a negative increment of temperature on the cooling curve. Inputs of the AND circuit 53 (FIG. 11) are connected to a unit output of the flip-flop 49 and to a zero output of the flip-flop 51.

Inputs of the AND circuit 54 are connected to a unit output of the flip-flop 50 and to a zero output of the flip-flop 52. A third input of each of the AND circuits 53 and 54 is connected to an output of the gate 48 for forming synchronizing clock pulses of the distributing element 43. The output of the gate 48 is also connected to one input of the gate 55 of the element 44 and to one input of the gate 56 of the element 45. The other inputs of each of the gates 55 and 56 are connected to unit outputs of the flip-flops 51 and 52, respectively. An output of the AND circuit 53 is connected to a unit input of the flip-flop 51, whereas an output of the AND circuit 54 is connected to a unit input of the flip-flop 52. An output of the gate 55 is connected to zero inputs of the flip-flops 49 and 51, and is an output 17 (FIG. 6) of the synchronizer 3, where there are applied synchronized code pulses corresponding to a positive increment of temperature on the cooling curve.

An output of the gate 56 (FIG. 11) is connected to zero inputs of the triggers 50 and 52, and is an output 18 (FIG. 6) of the synchronizer 3, where there are applied synchronized code pulses corresponding to a negative increment of temperature on the cooling curve.

Figure 12:
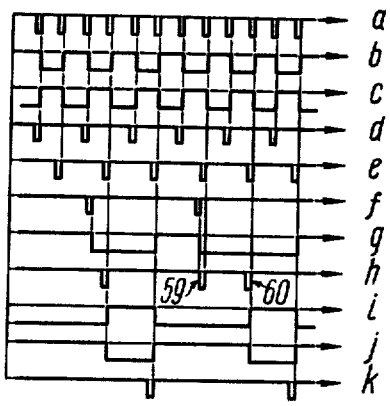

Shown in FIG. 12 are time plots illustrating the operation of the synchronization unit 3.

FIG. 13 shows an alternative embodiment of the selector 11 of signs of the thermal effect of phase transformation. The selector comprises a decoder 57 whose inputs are the inputs of the selector 11, and "OR" circuit 58 having its inputs connected to the outputs of the decoder. The output of the "OR" circuit 58 is at the same time the output 27 of the selector 11.

The device operates as follows. The signal carrying information on the temperature of the metal or alloy being cooled is delivered from the temperature sensor to the input 12 of the converter 1 of temperature into a digital pulse code. The signal converted into a digital pulse code is fed to the outputs 13 and 14 of the converter, with each elementary increment of temperature there are formed code pulses at one of the outputs 13, 14, depending on the sign of the temperature increment. These code pulses from one of the outputs 13, 14 are fed to the respective input of the synchronizer 3. Clock pulses from the output 15 of the clock pulse generator are also fed to the synchronizer 3. The synchronizer 3 provides for distribution in time of code and clock pulses which is needed to preclude malfunctioning of the device. Sychronized clock pulses arrive at the output 16 of the synchronizer and further at the count inputs of the cycle counter 7 and the time interval counter 9. Synchronized code pulses corresponding to the positive increment of temperature are fed from the output 17 of the synchronizer to the add inputs of the threshold counter 6 and the reversible counter 4. Synchronized code pulses corresponding to a negative increment of temperature are fed from the output 18 of the sychronizer 3 to the subtract inputs of the threshold counter 6 and the reversible counter 4. In the reversible counter a parallel code is formed of the metal current temperature. The threshold counter 6 provides for selection of local increments of temperature and is constructed so that at its overflow outputs 20, 21 pulses are formed each time when a number of code pulses being fed to its inputs corresponds to a certain threshold $\pm \epsilon_o$, i.e. at the overflow outputs 20, 21 of the threshold counter 6 pulses are formed providing there are certain positive or negative temperature increments of the metal, respectively. These pulses are applied to the initial setting inputs of the time interval counter 9 and to the control inputs of the main and the additional registers 5, 8. Pulses corresponding to negative increments of temperature are fed from the overflow output 21 to the count input of the temperature increment counter 10. Prior to the start of each measuring cycle, the cycle counter 7 is set to its initial state and, consequently, its contents in the process of a metal or an alloy cooling are proportional to the current time elapsed since the start of the temperature measuring cycle. As soon as the successive pulse is fed either from the overflow output 20 or 21 of the threshold counter 6 to the control inputs of the main register 5 and the auxiliary register 8, there is entered a code from the information output 22 of the cycle counter 7 into the main register 5, the code being proportional to the time that elapsed from the beginning of the cooling process till the moment when the threshold counter 6 is triggered. Similarly, from the information output 19 of the reversible counter 4, there is entered a code into the register 5, which is proportional to the temperature of the metal at the moment when the threshold counter 6 comes into action.

A code proportional to the time elapsed from the beginning of the measuring cycle, is continuously fed from the information output 23 of the auxiliary register 8 to the selector 11 input. A code proportional to the current temperature of a metal or an alloy being cooled, is continuously fed from the information output 26 of the main register 5 to the other input of the selector 11.

The temperature increment counter 10 provides for determining a temperature increment relative to the maximum temperature $T_{max}$ (FIG. 7) recorded during a temperature measuring cycle. Prior to the start of the temperature measuring cylcle the counter 10 (FIG. 6) is set to the initial state. On the portion O-A (FIG. 7) of the cooling curve, corresponding to a positive increment of temperature, pulses are formed only at the output 20 (FIG. 6) of the threshold counter 6. Consequently, no pulses are fed the count input of the temperature increment counter 10 and it retains its initial state.

On the portion A-B (FIG. 7), corresponding to a negative increment of temperature, pulses are fed from the overflow output 21 of the threshold counter 6 to the count input of the temperature increment counter 10. As a result, in this counter a code is formed proportional to a negative temperature increment of the metal or alloy being cooled, relative to the maximum temperature $T_{max}$ of the cooling curve.

Information from the information output 25 of the temperature increment counter 10 is continuously fed to the input of the selector 11 of signs of the thermal effect of phase transformation.

The time interval counter 9 provides for determining the time interval between two successive instants of time when a local increment of temperature assumes a predetermined value $\tau_o$. Each pulse which is formed at the overflow outputs 20, 21 of the threshold counter 6 sets the counter 9 to its initial state, whereupon the counter 9 starts a new time metering by calculating clock pulses. Information from the information output 24 of the counter 9 is continuously fed to the input of the selector 11 of signs of the thermal effect of phase transformation.

Thus, in the process of metal or alloy cooling the inputs of the selector 11 of signs of the thermal effect of phase transformation are continuously supplied with information on: the temperature T of a metal or an alloy, on the increment of temperature $\Delta T$ of a metal or an alloy, on the time t elapsed from the beginning of the temperature measuring cycle and on a value $\tau^*$ of the time interval elapsed since the successive moment when an increment of temperature has assumed the predetermined value. In this case, the information on values T, $\Delta T$ and t varies only at the moment when an increment of temperature assumes the predetermined value $\epsilon_o$.

The selector 11 of signs of the thermal effect is constructed so that a control signal is formed at the output 27 only when the time interval $\tau^*$ determined by the time interval counter 9, is equal to a threshold $\tau_o$ of the duration of a temperature stop, with said threshold being dependent on parameters T, $\Delta T$ and t according to the formula (1).

In the process of metal or alloy cooling, prior to occurrence of a temperature arrest (portions O-A and A-B of the cooling curve in FIG. 7), the threshold counter 6 will continuously reset the time interval counter 9 in its initial state so that the contents of the latter does not assume a value equal to a threshold $\tau_o$ of the duration of the temperature arrest. Consequently, at this stage of the process of cooling, no control signal is formed at the output of the selector 11 of signs of the thermal effect of phase transformation. If in the process of cooling there occurs temperature arrest whose positive or negative increment of temperature does not exceed $\epsilon_o$, the threshold counter 6 will not be overflown. If duration $\tau$ of the temperature arrest is such that the contents of the time interval counter 9 assumes a value equal to a threshold $\tau_o$ of the duration of the temperature arrest, determined by parameters T, $\Delta T$ and t calculated for the moment when the temperature arrest occurs, at the output 27 of the selector 11 of signs of the thermal effect of phase transformation a control signal is formed. This signal is fed to the count blocking inputs of the threshold counter 6 and the time interval counter 9, whereby excluding a possibility of the information alteration in the counters 9 and 10, and in the registers 5 and 8. As a result, a control signal at the output 27 of the selector 11 of signs of the thermal effect of phase transformation is retained till the successive measuring cycle. The appearance of this control signal is indicative of the presence of the thermal effect of phase transformation. The information stored in the main register 5 after formation of this control signal, represents a code of the liquidus temperature of a metal or an alloy. This information can be directly transmitted to the master computer, to the digital display unit, to the digital printer, etc. for representation of parameters of a metal or an alloy, for instance, to indicate the carbon content therein.

The operating of the converter 1 shown in FIG. 8 is illustrated by the time plots in FIGS. 9, 10.

The movement of a sliding contact 35 (FIG. 8) of an automatic potentiometer 36 is parallel to that of a holder 34 of the converter 1. The light flux of a dial lamp 33, incident on photodiodes 31 and 32, is modulated by marks 29 and 30 of a measuring scale 28.

Signals from the photodiodes 31 and 32 are applied to the inputs of Schmitt trigger 37 and 38, respectively.

When the slide contact 35 is moving from left to right, the signal (FIG. 9a) of the photodiode 31 (FIG. 8) lags by a quarter of a period behind the signal (FIG. 9b) of the photodiode 32 (FIG. 8). In this case the signal (FIG. 9c) at the unity output and the signal (FIG. 9d) at the zero output of the Schmitt trigger 37 (FIG. 8) lags by a quarter of a period behind the signal (FIG. 9e) at the unity output and the signal (FIG. 9f) at the zero output of the Schmitt trigger 38 (FIG. 8), respectively.

A pulse shaper 39 forms pulses (FIG. 9g) on the positive front side of the signal (FIG. 9e) arriving from the unity output of the Schmitt trigger 38 (FIG. 8). A pulse shaper 40 forms pulses (FIG. 9h) on the positive front side of the signal (FIG. 9f) arriving from the zero output of the Schmitt trigger 37 (FIG. 8).

The pulses (FIG. 9g) are fed to the pulse input of a gate 41 from the output of the signal shaper 39 (FIG. 8). The pulses (FIG. 9h) are fed to the pulse input of the gate 42 from the zero output of the signal shaper 40 (FIG. 8). The signals (FIG. 9d) are fed to the control inputs of the gate 41 and the gate 42 from the zero output of the Schmitt trigger 37 (FIG. 8). In this case, as is seen from the timing chart (FIG. 9), at the moment when signals are applied to the pulse input of the gate 41 (FIG. 8), the gate 41 is locked because there is applied an inhibitory signal to its control input from the zero output of the Schmitt trigger 37. At moment when signals are applied to the pulse input of the gate 42, the gate 42 is open because there is applied a permitting signal to its control input from the zero output of the Schmitt trigger 37.

At the same time, as the sliding contact 35 (FIG. 8) moves from left to right, no signals (FIG. 9i) are formed at the output of the gate 41 (FIG. 8). The signals (FIG. 9j) at the output of the gate 42 (FIG. 8) are code pulses of the converter 1, corresponding to a positive increment of temperature on the cooling curve.

When the sliding contact 35 (FIG. 8) is moving from right to left, the signal (FIG. 10a) of the photodiode 31 (FIG. 8) is a quarter of a period ahead of the signal (FIG. 10b) of the photodiode 32 (FIG. 8). In connection with this, at moments when the pulses (FIG. 10g) from the pulse shaper 39 (FIG. 8) are applied to the pulse input of the gate 41, permitting signals (FIG. 10d) are fed to the control input of the gate 41 from the zero output of the Schmitt trigger 37 (FIG. 8). At moments when pulses (FIG. 10h) arrive from the pulse shaper 40 (FIG. 8) to the pulse input of the gate 42, inhibitory signals (FIG. 10d) are fed to the control input of the gate 42 from the zero output of the Schmitt trigger 37 (FIG. 8).

At the same time, as the sliding contact 35 (FIG. 8) moves from right to left, no signals (FIG. 10j) are formed at the output of the gate 42 (FIG. 8). The signals (FIG. 10i) at the output of the gate 41 (FIG. 8) are code pulses of the converter 1, corresponding to a negative increment of temperature on the cooling curve.

The operating principle of the synchronizer 3 shown in FIG. 11 is illustrated by the timing charts in FIG. 12.

When clock pulses (FIG. 12a) are fed from the generator 2 (FIG. 6) to the count input of the flip-flop 46 (FIG. 11) of the clock pulse distributing element 43, the flip-flop successively changes its state. Signals from the unity output (FIG. 12c) and zero output (FIG. 12b) of the flip-flop 46 (FIG. 11) are applied to the control inputs of the gates 47 and 48, respectively. The pulse inputs of these gates are fed with the clock pulses (FIG. 12a) from the generator 2 (FIG. 6). As a result, at the outputs of the gates two pulse trains are formed shifted in time relative to each other. In this case, at the output of the gate 47 (FIG. 11) there are formed synchronized clock pulses (FIG. 12d), whereas at the output of the gate 48 (FIG. 11) there are formed synchronizing clock pulses (FIG. 12e).

The repetition frequency $f_1$ of the synchronized clock pulses is equal to the repetition frequency $f_2$ of the synchronizing clock pulses which is $$f_1 = f_2 = \tfrac{1}{2} f_o \qquad (2)$$

where $f_o$ is the repetition frequency of the pulses arriving from the output 15 (FIG. 6) of the clock pulse generator 2.

The synchronized clock pulses are applied to the output 16 of the synchronizer 3.

The synchronizing clock pulses are applied to the inputs of the AND circuit 53 (FIG. 11) and to the inputs of the gate 55 of the synchronizing element 44, as well as to the inputs of the AND circuit 54 and to the inputs of the gate 56 of the synchronizing element 45.

In the initial state, all the flip-flops 49, 50, 51, 52 are zeroed by an initial setting key not shown in FIG. 11. When from an output of a converter 1 (FIG. 6) a code pulse (FIG. 12f) arrives corresponding to the positive increment of temperature on the cooling curve, the flip-flop 49 (FIG. 11) is set in the unity state (FIG. 12g). After the state of the flip-flop 49 has been changed (FIG. 11), at the moment when a successive synchronizing clock pulse is applied, a pulse (FIG. 12h) appears at the output of the AND circuit 53. This pulse will set the buffer flip-flop 51 (FIG. 11) in the unity state (FIG. 12j) thus opening the gate 55 (FIG. 11). At the moment of arrival of a successive synchronizing clock pulse (FIGS. 12e, i) at the output of the gate 55 (FIG. 11) a synchronized code pulse (FIG. 12k) is formed corresponding to a positive increment of temperature. This pulse is applied to the output 17 (FIG. 6) of the synchronization unit 3 and to the inputs of trigger 49 and 51 (FIG. 11). In this case, the signal (FIG. 12i) arriving from the zero output of the flip-flop 51 (FIG. 11) at one of the inputs of the AND circuit 53 precludes the arrival of the signal at the unity input of the flip-flop 51 at the moment, when a pulse is applied to the zero input of the trigger 51. The formed synchronized code pulse sets flip-flops 49 and 51 to a zero state, thus preparing the synchronizing element 44 for receiving the next code pulse.

During operation of the synchronizing element 44, the code pulse may partially coincide in time with the synchronizing clock pulse. This may result in an inadequate pulse 59 (FIG. 12h) at the output of the AND circuit 53 (FIG. 11), for example, a pulse having an insufficient duration or amplitude. When such inadequate pulse occurs, the buffer flip-flop 51 may continue to remain in the zero state until there is applied another synchronizing clock pulse to the input of the AND circuit 53. In so far as at the moment of the arrival of the next synchronizing clock pulse, the flip-flop state can not change any longer, at the output of the AND circuit 53 at the instant in time there appears a second (adequate) pulse 60 (FIG. 12h). This pulse sets the flip-flop 51 (FIG. 11) in the unity state. At the moment of arrival of a successive synchronizing clock pulse (FIG. 12e), at the output of the gate 55 a synchronized code pulse (FIG. 12k) is formed which is applied to the output 17 (FIG. 6) of the synchronizer 3 with simultaneous setting the flip-flop 49 and 51 in the zero state.

In a similar way at the outut of the gate 56 of the synchronizing element 45, there are synchronized code pulses formed corresponding to a negative increment of temperature. These pulses are fed to the output 18 (FIG. 6) of the synchronization unit 3.

Thus, the coincidence in time of the pulses formed at the outputs of the gates 55 and 56 (FIG. 11) with the pulses arriving from the output of the gate 48 of the pulse distributing element 43 ensures division in time of the synchronized clock pulses and the synchronized code pulses.

To provide reliable operation of the synchronizer 3, it is necessary that the repetition frequency $f_2$ of the synchronizing clock pulses should be two or three times greater than the maximum repetition frequency $f_{3\,max}$ of the code pulses arriving from the output of the converter (FIG. 6), i.e.

$$f_2 \geq 3 f_{3\,max} \qquad (3)$$

Hence the pulse frequency at the output of the generator 2 must be $$f_o = 2 f_2 \geq 6 f_3 \qquad (4)$$

The selector 11 of signs of the thermal effect of phase transformation, shown in FIG. 13, operates as follows. In the process of the metal or alloy cooling, the code combinations from the information outputs (digit outputs) of the registers 5,8 and of the counters 9 and 10, are fed to the inputs of the decoder 57. As soon as any of the code combinations of the parameters T, ΔT, t, and τ* satisfying formula (1), is applied to the inputs of the decoder 57 at one of the outputs of the decoder 57 there is formed a signal being fed, through the "OR" circuit, to the output 27 of the selector 11.

The employment in the aggregate of main parameters of the process of cooling of metal or alloy, allows the temperature arrests caused both by the thermal effect and by the pseudothermal effect to be distinguished even in such cases when these temperature arrests are of the equal duration, which, as a whole, improves reliability of discriminating the thermal effect of phase transformation.

We claim:

1. A method for discriminating the thermal effect of phase transformation of metals and alloys in the process of their cooling, comprising the steps of:

cooling the metal or alloy at a measured temperature;

establishing an increment of said temperature relative to a maximum temperature recorded during temperature measurement;

calculating a threshold of duration of a temperature arrest after time elapsed since the start of temperature measurement; making a decision ascertaining the occurrence of the thermal effect of phase transformation, said threshold being calculated as a function of (a) the temperature of the metal or alloy being cooled, (b) an increment of said temperature relative to the maximum temperature recorded during the temperature measuring cycle, and (c) the time elapsed since the start of said temperature measuring cycle;

cooling metal or alloy and measuring the duration of the temperature arrest during cooling;

comparing the measured duration of the temperature arrest with the threshold value of the duration of the temperature arrest calculated for the moment when said temperature arrest occurs;

and ascertaining the occurrence of the thermal effect of phase transformation when measured duration of temperature arrest exceeds predetermined threshold of the duration of temperature arrest.

2. An apparatus for discriminating the thermal effect of phase transformation of metals and alloys in the process of their cooling, comprising: a converter for converting temperature into a digital pulse code, said converter having an input to which there is applied a signal carrying information relative to temperature of a metal or alloy being cooled; a first output for code pulses corresponding to a positive increment of temperature; a second output for code pulses corresponding to a negative increment of temperature; a clock pulse generator having an output; a synchronization unit for distributing in time code a clock pulses, having first and second inputs respectively connected to said first and second outputs of said converter for converting temperature into digital pulse code; a third input connected to said output of said clock pulse generator; a first output for code pulses corresponding to a positive increment of temperature, a second output for synchronized code pulses corresponding to a negative increment of temperature; an output of synchronized clock pulses; a reversible counter for generating a parallel temperature code, having an add input connected to said first output of said synchronization unit, a subtract input connected to said output of said synchronization unit, and an information output; a threshold counter for determining local increments of temperature, having an add input connected to said first output of said synchronization unit, a subtract input connected to said second output of said synchronization unit, an input for count blocking, a first overflow output for delivering pulses at the instant of time when the positive increment of temperature assumes a predetermined value, a second overflow output for delivering pulses at the instant of time when a negative increment of temperature assumes a predetermined value;

a cycle counter for determining the time elapsed since start of the temperature measuring cycle, having a count input connected to said output of synchronized clock pulses of said synchronization element, an information output of a parallel code of the time interval elapsed since the start of the temperature measuring cycle;

a first register for storing a parallel code of metal or alloy temperature at a successive instant of time when the increment of temperature assumes a predetermined value, having an information input connected to digit outputs of said reversible counter, a first and a second control inputs, and an information output;

a second register for storing a parallel code of the time interval elapsed since the start of the temperature measuring cycle until the next successive moment when the increment of temperature assumes a predetermined value, having an information input connected to said information output of said cycle counter, a first and a second control inputs, and an information output;

a counter of time intervals for determining the time metered from the next successive moment when a local increment of temprature assumes a predetermined value, and having a count input connected to said output of synchronized clock pulses of said synchronization unit, a first input of initial setting combined with said first control inputs of said first and second registers, being connected to said overflow output of said threshold counter, a second input of initial setting combined with said second control inputs of said first and second registers being connected to said second overflow output of said threshold counter, a count blocking input, an information output;

a temperature increment counter for determining an increment of temperature relative to the maximum temperature recorded during the temperature measuring cycle, having a counting input connected to said second overflow output of said threshold counter, and an information output;

a selector of signs of the thermal effect of phase transformation, having a first input connected to said information output of said first register, receiving therefrom information on the current temperature, a second input connected to said information output of said counter of temperature increments, receiving therefrom information on the current negative increment of temperature relative to the maximum temperature recorded during the measuring cycle, a third input connected to said information output of said second register and receiving therefrom information on the time interval elapsed since the start of the temperature measuring cycle, a fourth input connected to said information output of said time interval counter and receiving therefrom information on the time being metered from the next successive moment when the increment of temperature assumes as predetermined value, and an output for delivering a signal at the moment when the decision on the presence of the thermal effect of phase transformation is taken, connected to said count clocking inputs of said time interval counter and said threshold counter.

* * * * *